United States Patent [19]

Biswas

[11] Patent Number: 5,036,867

[45] Date of Patent: Aug. 6, 1991

[54] URINARY INCONTINENCE DEVICE

[75] Inventor: Nicholas Biswas, Blacktown, Australia

[73] Assignee: Zedlani Pty. Limited, Parramatta, Australia

[21] Appl. No.: 448,166

[22] Filed: Dec. 8, 1989

Related U.S. Application Data

[63] Continuation-in-part of Ser. No. 108,276, Oct. 13, 1987, Pat. No. 4,920,986.

[30] Foreign Application Priority Data

Oct. 14, 1986 [AU] Australia .................... PH8486

[51] Int. Cl.⁵ .................... A61F 5/48; A61F 2/02
[52] U.S. Cl. .................... 128/885; 600/30
[58] Field of Search .................... 600/28, 29, 30; 128/831, 833, 839, 885

[56] References Cited

U.S. PATENT DOCUMENTS

| | | | |
|---|---|---|---|
| 186,469 | 1/1877 | Fowler | 128/834 |
| 1,790,801 | 2/1931 | Dickstein | 128/834 |
| 2,574,767 | 11/1951 | Stubbs | 128/834 |
| 2,649,086 | 8/1953 | Sluijter | 600/29 |
| 3,554,184 | 1/1971 | Habib | 128/DIG. 25 |
| 3,646,929 | 3/1972 | Bonnar | 128/DIG. 25 |
| 3,705,575 | 12/1972 | Edwards | 600/29 |
| 3,841,304 | 10/1974 | Jones | 600/29 |
| 4,019,498 | 4/1977 | Hawtrey | 600/29 |
| 4,139,006 | 2/1979 | Corey | 600/29 |

*Primary Examiner*—Robert A. Hafer
*Assistant Examiner*—Michael Brown
*Attorney, Agent, or Firm*—Ladas & Parry

[57] ABSTRACT

An intra-vaginal device to aid in controlling urinary incontinence, the device includes a central portion (12) of an arcuate configuration to be positioned within the vagina in an upwardly convex orientation, a pair of rearward projections (22) which engage the posterior vaginal wall, a pair of forward projections (18) which engage the anterior vaginal wall adjacent the bladder neck to lift the bladder adjacent thereto, a bladder neck cradle (20) to cradle the bladder neck, with the device being formed of resilient material so as to flex into engagement with the vaginal wall to be retained in position.

9 Claims, 6 Drawing Sheets

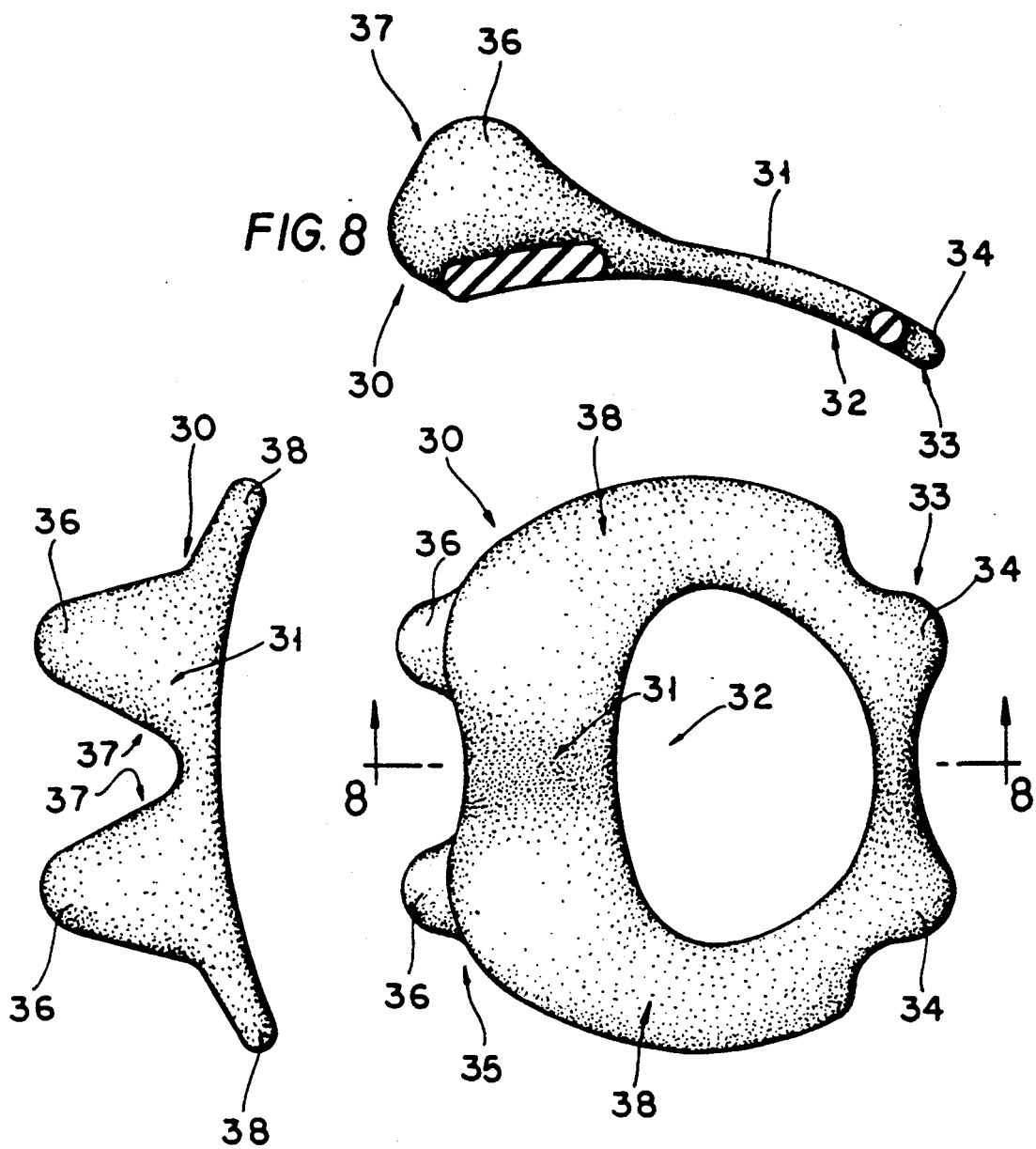

URINARY INCONTINENCE DEVICE

This is a continuation-part of copending application Ser. No. 07/108,276 filed on Oct. 13, 1987, now U.S. Pat. No. 4,920,986.

The present invention relates to devices for controlling urinary incontinence and to vaginal and rectal prolapse in females. Particularly, the invention relates to a device which may be removably inserted into the vagina.

Female urinary incontinence is a common problem and is particularly prevalent where damage to the bladder or neck of the bladder has occurred during child birth. In elderly female patients urinary incontinence is wide spread.

In normal continent patients, in the erect posture, there is no descent of the bladder neck below the pelvic floor muscle, thereby equal distribution of intra-abdominal pressure to the bladder and bladder neck and pelvic urethra occurs, and continence is maintained. However, in stress incontinence this is lost due to descent of the bladder neck below the pelvic floor muscle. On coughing or sneezing or physical exercise, i.e. when strain is put upon the bladder, an involuntary spurt of urine is released from the bladder. This involuntary urine release is unpleasant and embarrassing. The released urine may irritate the groin region and result in an offensive odour.

Vaginal and rectal prolapse are quite common conditions in females, particularly those who have vaginally delivered one or more children. These conditions may be painful, and uncomfortable. Additionally, sexual intercourse may be impaired by occlusion of the vagina.

It is a generally accepted view that surgical treatment is most appropriate for cure of stress incontinence and vaginal and rectal prolapse. However, in elderly or infirm patients the risk of surgery is too great, so that often these conditions go untreated.

Previously proposed devices to treat incontinence and avoid recourse to surgery have generally been unsatisfactory. Particularly, they are cumbersome, difficult to use, need to be replaced frequently, are inadequate in cases of permanent incontinence and often fail to prevent involuntary urinary leakage.

A previously known intra-vaginal device for controlling urinary incontinence in females is disclosed in U.S. Pat. No. 4,139,006. This previously known device has as its object the deflection of the urethra. More particularly it has the object of displacing a surface of the superior wall of the vagina, and an intermediate section of the urethra adjacent thereto, toward to pubic bone, to reduce the urethro-visicle angle to restore the patient's natural control over the flow of urine through the urethra from the bladder to the urethral opening. The device has a pair of forward projections which lie on either side of the urethra intermediate portion and apply a force thereto to deflect the intermediate portion of the urethra toward the pubic bone.

One aspect of the present invention has as its object to provide an intra-vaginal device to aid in controlling vaginal and rectal prolapse.

There is disclosed herein an intra-vaginal device, comprising a forward and a rearward portion interconnected by a base central portion, the forward portion being adapted to lie adjacent the anterior vaginal wall and including a projection means to lift the bladder base and bladder neck, lying behind the vaginal wall, said forward portion further including a hollow within which the bladder neck is to rest, the rearward portion being adapted to lie adjacent the posterior vaginal wall, and wherein said device is resiliently deformable enabling resilient deformation into an arcuate configuration so that within the vagina it resiliently deflects into engagement with the vaginal wall.

The base portion is preferably arch shaped, and is preferably comprised of a resilient material or has resilient material embedded within the arch.

Preferably, the cradle-like structure, which lifts the bladder base and bladder neck, is formed by two protrusions extending from the free end of the limb which lies adjacent the anterior vaginal wall. These protrusions have a depression therebetween. This depression accommodates the anterior vaginal wall and the neck and base of the bladder.

In use, the base portion biases the limbs outwardly to aid in retention of the device in the vagina.

The limb adjacent the posterior vaginal wall preferably has two legs at its free end. These legs are preferably curved and splayed in order to fit over the perineal body for supporting the device in the vagina.

Preferably, the opposing inner surfaces of the two limbs, are covered by a spongy deformable material bearing complementary grooves and ridges. This material imitates vaginal mucosa. Sexual intercourse is therefore not effected by the device as the spongy material cannot readily be distinguished by the male partner. Additionally, the grooves and ridges aid in channelling menstrual blood and vaginal secretions through the vagina.

A further aspect of the present invention has the object of providing an intra-vaginal device to aid in controlling urinary incontinence.

There is disclosed herein an intra-vaginal device to aid in controlling urinary incontinence in females, said device having a central portion of an arcuate cupped configuration and shaped to be retained, within the vagina of a user, in an upwardly convex configuration, a rearward portion extending rearwardly from said central portion to engage the posterior vaginal wall, a forward portion extending upwardly from said central portion to engage the anterior vaginal wall adjacent the bladder neck and to lift the bladder portion located adjacent thereto, a bladder neck cradle provided by said forward portion positioned to cradle the bladder neck, and wherein said device is formed of resiliently deformable material so as to flex into engagement with the posterior and anterior vaginal wall to retain the device in its upwardly convex position with the forward portion lifting the bladder and cradling the bladder neck.

Still further, it is preferred that the above described ring would be adjustable in diameter.

The present invention will now be described by way of example only with reference to the following drawings in which:

FIG. 7 is a schematic bottom plan view of a further intra-vaginal device to aid in controlling urinary incontinence;

FIG. 8 is a schematic sectioned side elevation of the device of FIG. 7 sectioned along the line 8—8; and FIG. 9 is a schematic end elevation of the device of FIG. 7.

Figure 1:
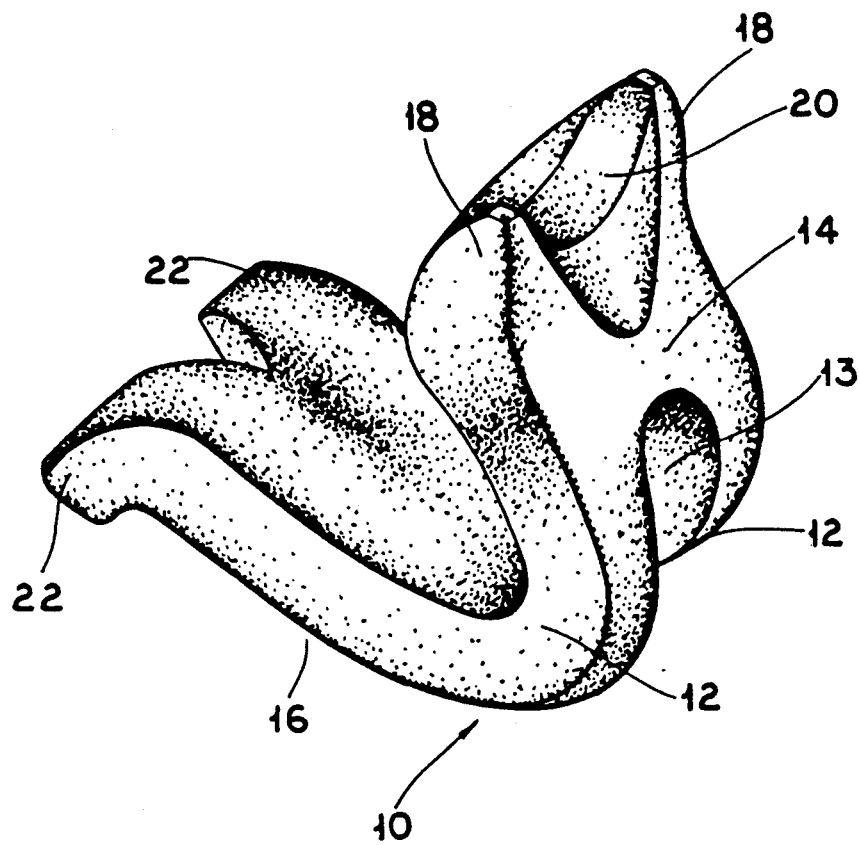
FIG. 1 is a perspective view of the intra-vaginal device.
Figure 2:
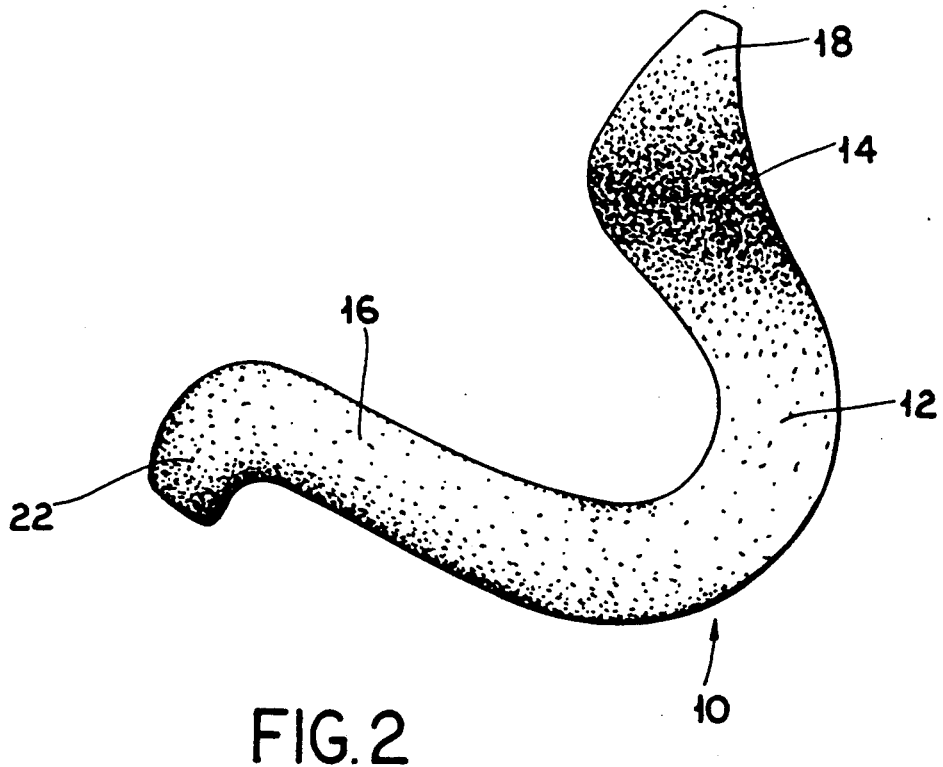
FIG. 2 is a side view of the intra-vaginal device.
Figure 3:
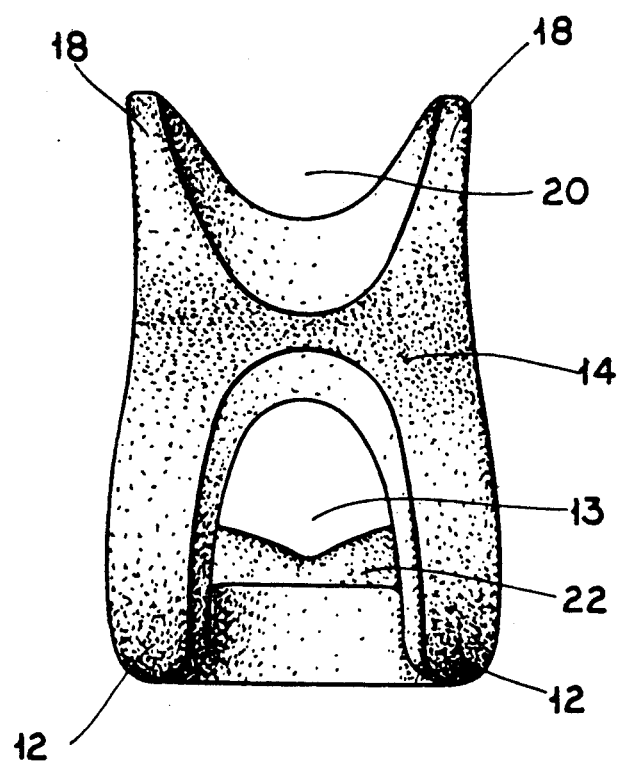
FIG. 3 is an end view of the intra-vaginal device.

The intra-vaginal device shown in FIG. 1 is constructed of a flexible material, for example a plastic/silicone compound.

The device comprises a base portion 10 which is of an arcuate form. In this embodiment the base portion forms an arch 12 of generally "U-shaped" configuration. The base portion 10 may be inherently resilient or may contain a resilient insert. The arch 12 contains an aperture 13 which in use is adjacent the cervix of the uterus. The arch 12 interconnects two opposing limbs 14 and 16. The limb 14 lies adjacent the anterior vaginal wall in use and has at its end two opposed rounded projections 18 having a depression 20 therebetween to form a cradle-like structure.

The limb 16 extending from the arch 12 is of substantially planar construction and has at its forward end a pair of splayed legs 22.

The flexible and resilient nature of the arch 12 enables the device to be readily inserted into the vagina and aids in its retention therein. Particularly, the arch 12 bases the limbs 14 and 16 outwardly, causing them to press against the anterior and posterior walls of the vagina respectively, this holding the device in place.

Figure 4:
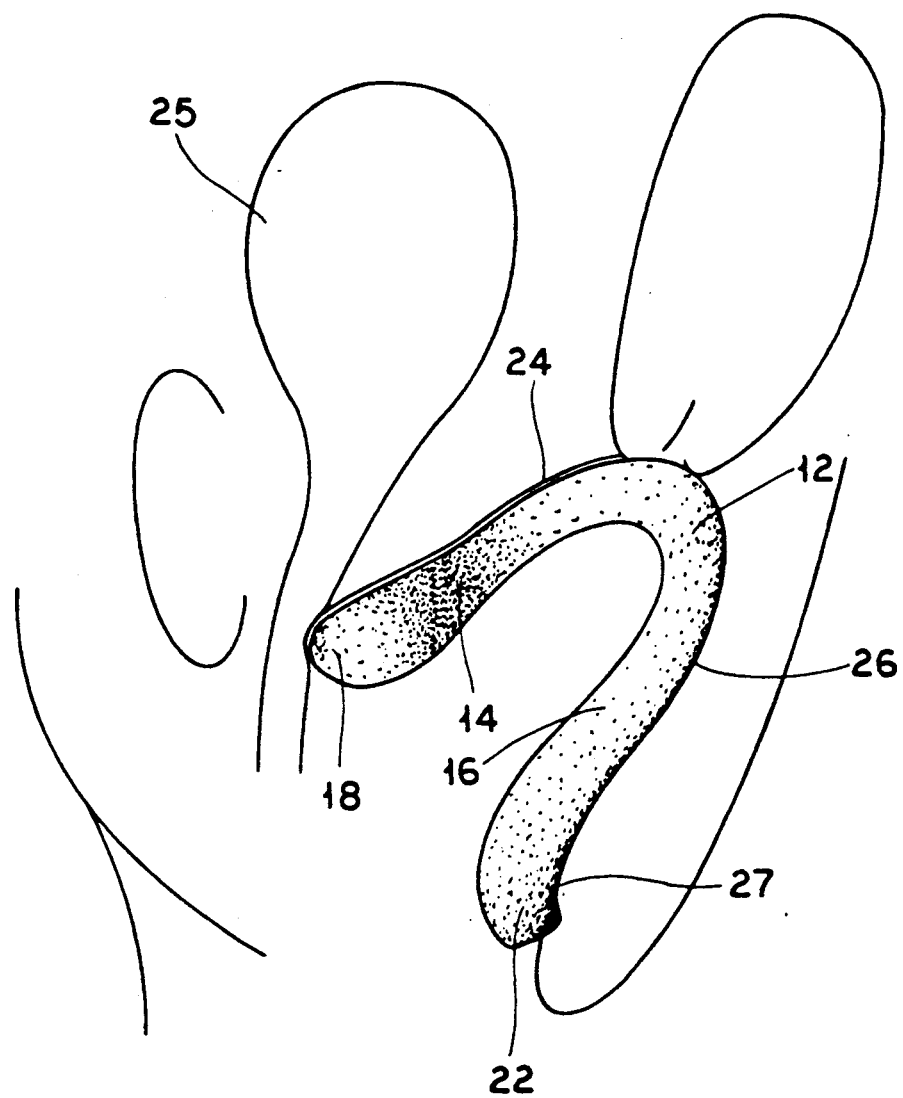
FIG. 4 is a schematic view of a saggital section of the female pelvic organs showing the intra-vaginal device in place.

As shown in FIG. 4, when the device is inserted into the vagina, the limb 14 lies adjacent to and supports the anterior vaginal wall 24 preventing prolapse of the anterior vaginal wall (cystocele) and prolapse caused by the bladder 25 pressing against the anterior vaginal wall 24 (cysto-urethrocele). The outward bias of the limb 14 causes the projections 18 to cradle the anterior vaginal wall 24 and lift the neck and base of the bladder above the pelvic floor muscle thereby causing continence. Additionally a significant closure of the bladder neck is achieved as is a reduction of the included angle between the urethra and the bladder. These features again increase continence.

The arch 12 supports the cardinal and uterosacaral ligaments (not shown) and helps to lift the uterus in the pelvic cavity thereby preventing uterine prolapse. The aperture 13 in the arch 12 lies adjacent the cervix of the uterus.

The limb 16 lies adjacent to and supports the posterior vaginal wall 26, thereby preventing prolapse of the posterior vaginal wall 26 (enterocele) and rectal prolapse (retocele). The legs 22 of the limb 14 rest on the posterior vaginal wall 26 in the region of the para-rectal fossa 27. The splayed nature of the legs enables them to fit over the perineal body, this aiding in retention of the device in the vagina.

The device may be of different sizes to accommodate different vaginal size. Preferably, those portions of the device contacting the vaginal wall are smeared with Disaestrol and Sultril cream in order to minimize vaginal irritation.

Figure 5:
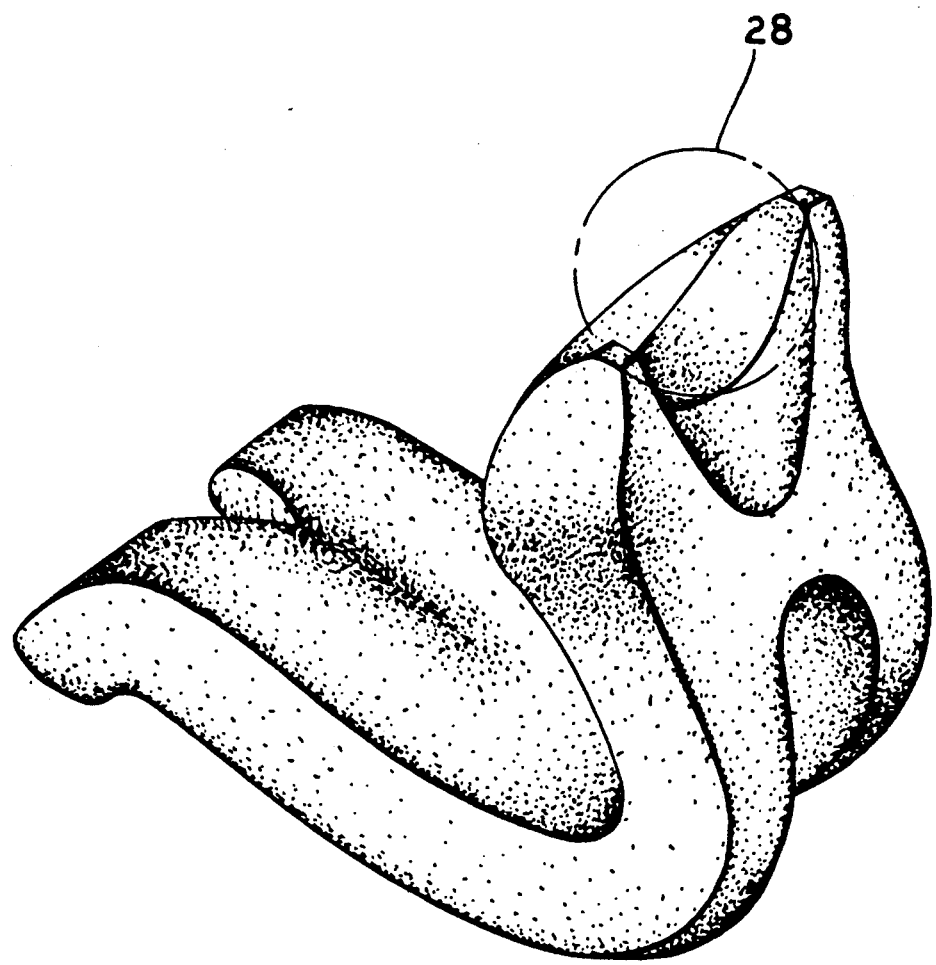
FIG. 5 is a schematic perspective view of an intra-vaginal device to aid in controlling urinary incontinence.
Figure 6:
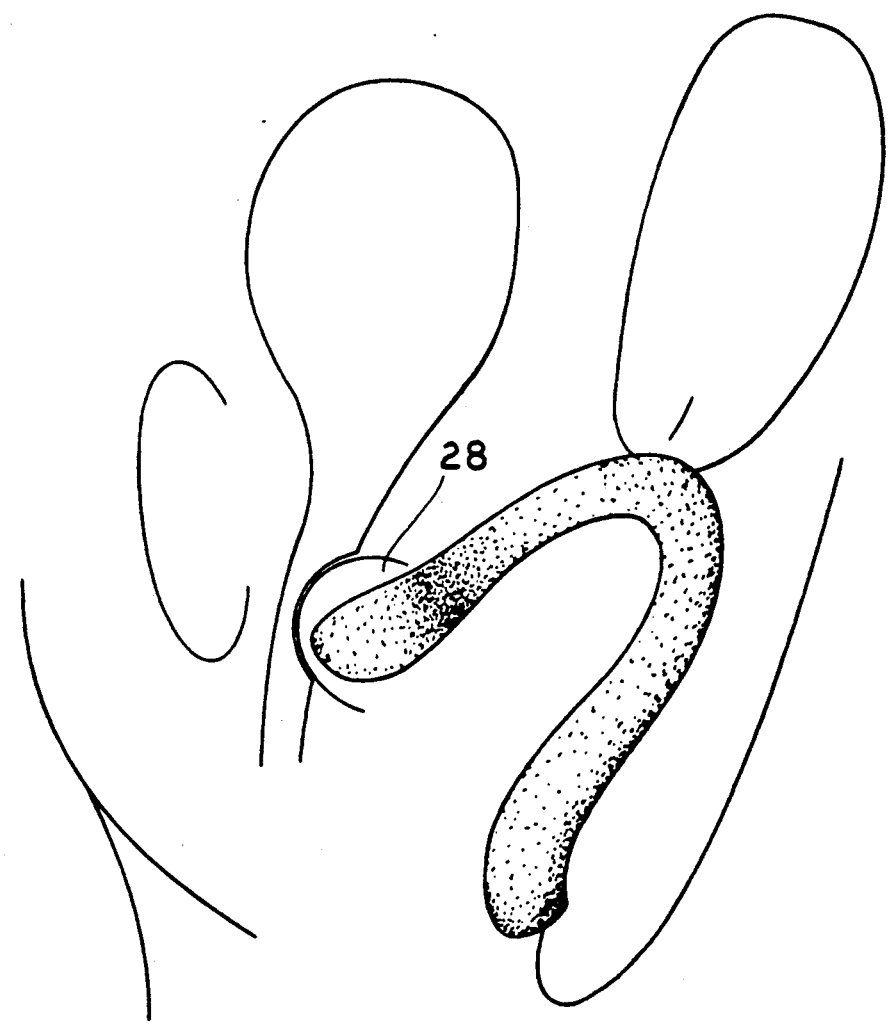
FIG. 6 is a schematic view of a saggital section of the female pelvic organs showing the device of FIG. 5 in place.

In a further embodiment of the present invention as shown in FIGS. 5 and 6, a small inflatable balloon 2B may be provided between the projections 18. The balloon may be inflated to compress the bladder neck against the public symphasis thus closing off the urethra resulting in continence. The balloon 28 may be inflated/deflated by virtue of a small lead connected to the balloon which passes out of the vagina where it can be manipulated by the patient.

In FIGS. 7 to 9 there is schematically depicted an intra-vaginal device to aid in controlling urinary incontinence. The device 30 is formed of resilient material so that in use it is resiliently deformed within the vagina so as to be biased outward into contact with the posterior and anterior vaginal wall. The device is about 8 cm in diameter. The device 30 includes a central portion 31 of cupped configuration, i.e. similarly arcuate in first and second perpendicular, lateral directions on one side and convex on the opposite side, having an aperture 32 to allow for the discharge of menstrual blood and vaginal secretions.

Extending rearwardly from the central portion 31 is a rear portion 33 which in this particular embodiment comprises a pair of rearwardly extending projections 34.

Also extending from the central portion 31, is a forward portion 35 which projects generally upwardly and in use, extends both forwardly and upwardly to engage the anterior vaginal wall adjacent the bladder neck. The forward portion 35 includes a pair of upwardly extending projections 36 which engage the anterior vaginal wall to lift the bladder adjacent the bladder neck. The projections 36 are about 2 cm high. Defined between the portions 36 is a cradle 37 within which the bladder neck lies to be cradled thereby. It should be appreciated that the pressures applied to the bladder neck are minimized by the cradle neck 37.

Preferably the device 37 would be integrally formed of moulded elastomeric material having sufficient resilience so that upon being deformed and inserted in the vagina, the rear portion 33 and forward portion 35 are resiliently biased into contact with the posterior and anterior wall of the vagina.

The central portions 31 have sides 3B which also engage the sides of the vaginal wall to aid in retaining the device 30 in position, that is concaved upwardly so that the forward portion 36 engages the anterior vaginal wall adjacent the bladder.

In the above embodiment the device 30 is preformed so as to be "cup" shaped. However, the central portion 31 could be of a more planar configuration, so that in position within the vagina it is resiliently deformed into an arcuate or "cup" shaped configuration.

The above discussed preferred embodiments of the present invention have the advantage that they may be placed in position by a medical practitioner without anaesthetic, with immediate results achievable.

What is claimed is:

1. In an entirely intra-vaginal device aid in controlling incontinence in females, the improvement of said device comprising a central portion of an arcuate cupped configuration and shaped to be retained, within the vagina of a user, in an upwardly convex orientation, a rearward portion extending rearwardly from said central portion to engage the posterior vaginal wall, a forward portion extending upwardly from said central portion to engage the anterior vaginal wall adjacent the bladder neck and to lift the bladder portion located adjacent thereto, a bladder neck cradle which is a depression provided at the top of said forward portion positioned to cradle the bladder neck, and wherein said device is formed of resiliently deformable material so as to flex into engagement with the posterior and anterior vaginal wall to retain the device in its upwardly convex position with the forward portion lifting the bladder and cradling the bladder neck.

2. The device claim 1 wherein said rear portion is a pair of rearwardly extending projections, and said forward portion is a pair of upwardly extending projections, between which said cradle is located.

3. The device of claim 2 wherein said central portion has an aperture to provide for the discharge of menstrual blood and vaginal secretions.

4. The device of claim 3 wherein said device is integrally moulded from elastomeric material.

5. In an entirely intravaginal urinary incontinence device, the improvement comprising a resilient annular body defining an annulus, the annular body having integrally formed on respective portions thereof two projections that project, at least in part, correspondingly transversely to the annulus of the annular body, the projections defining therebetween a cradle for engaging the anterior vaginal wall and lifting the bladder adjacent the bladder neck.

6. The device of claim 5 wherein the annulus is planar.

7. The device of claim 5 wherein the two projections extend exteriorly beyond the exterior periphery of the annular body.

8. The device of claim 5 wherein the two projections extend exteriorly beyond the exterior periphery of the annular body.

9. In an entirely intra-vaginal device to aid in controlling incontinence in females, the improvement of the device, comprising:

a resilient central member having aperture means comprising an aperture through the central member for allowing the discharge of menstrual blood and vaginal secretions through the central member when the central member is in a vagina, the central member being upwardly convex on one side and of cupped configuration on an opposite side at least when the central member is in the vagina; and forward-portion cradle means comprising two, spaced, upward projections from the one side of the central member at one, forward end thereof that form therebetween a cradle depression for engaging one side of an anterior wall of the vagina when the central member is in the vagina and lifting a bladder on an opposite side of the anterior wall adjacent a neck of the bladder.

* * * * *

UNITED STATES PATENT AND TRADEMARK OFFICE
CERTIFICATE OF CORRECTION

PATENT NO. : 5,036,867
DATED : August 6, 1991
INVENTOR(S) : Nicholas Biswas

It is certified that error appears in the above-identified patent and that said Letters Patent is hereby corrected as shown below:

Title page, Item 63, after "4,920,986" insert -- and PCT/AU88/00110 filed April 14, 1988 --.

Column 1, line 6, after "4,920,986" insert -- and International Application PCT/AU88/00110 filed on April 14, 1988 and which designated the U.S. --.

Signed and Sealed this

Sixteenth Day of March, 1993

Attest:

STEPHEN G. KUNIN

Attesting Officer

Acting Commissioner of Patents and Trademarks